(12) United States Patent
Hancu

(10) Patent No.: US 6,399,794 B1
(45) Date of Patent: Jun. 4, 2002

(54) DIRECT EPOXIDATION PROCESS USING CARBONATE MODIFIERS

(75) Inventor: Dan Hancu, Secane, PA (US)

(73) Assignee: Arco Chemical Technology, L.P., Houston, TX (US)

( * ) Notice: Subject to any disclaimer, the term of this patent is extended or adjusted under 35 U.S.C. 154(b) by 0 days.

(21) Appl. No.: 09/998,939

(22) Filed: Nov. 15, 2001

(51) Int. Cl.⁷ .............................................. C07D 301/06
(52) U.S. Cl. ...................................... 549/533; 549/532
(58) Field of Search ................................. 549/533, 532

(56) References Cited

U.S. PATENT DOCUMENTS

| | | | |
|---|---|---|---|
| 3,351,635 A | 11/1967 | Kollar | 260/348.5 |
| 4,367,342 A | 1/1983 | Wulff et al. | 549/529 |
| 4,410,501 A | 10/1983 | Taramasso et al. | 423/326 |
| 4,833,260 A | 5/1989 | Neri et al. | 549/531 |
| 5,859,265 A | 1/1999 | Müller et al. | 549/531 |
| 6,008,388 A | 12/1999 | Dessau et al. | 549/531 |

FOREIGN PATENT DOCUMENTS

JP    4-352771    12/1992

*Primary Examiner*—Ba K. Trinh
(74) *Attorney, Agent, or Firm*—Kevin M. Carroll

(57) ABSTRACT

The invention is a process for epoxidizing an olefin with hydrogen and oxygen in the presence of a modifier and a catalyst comprising a noble metal and titanium zeolite. The modifier is (a) calcium carbonate in the presence of carbon dioxide or (b) ammonium bicarbonate. The process results in increased catalyst activity, selectivity to epoxide, and increased catalyst life.

18 Claims, No Drawings

DIRECT EPOXIDATION PROCESS USING CARBONATE MODIFIERS

FIELD OF THE INVENTION

This invention relates to an epoxidation process using a carbonate-containing modifier. The process comprises reacting olefin, hydrogen, and oxygen in the presence of a modifier and a catalyst comprising a noble metal and a titanium zeolite. The modifier is (a) calcium carbonate in the presence of carbon dioxide or (b) ammonium bicarbonate. Surprisingly, the process results in higher activity and selectivity to epoxide, as well as increased catalyst life.

BACKGROUND OF THE INVENTION

Many different methods for the preparation of epoxides have been developed. Generally, epoxides are formed by the reaction of an olefin with an oxidizing agent in the presence of a catalyst. The production of propylene oxide from propylene and an organic hydroperoxide oxidizing agent, such as ethyl benzene hydroperoxide or tert-butyl hydroperoxide, is commercially practiced technology. This process is performed in the presence of a solubilized molybdenum catalyst, see U.S. Pat. No. 3,351,635, or a heterogeneous titania on silica catalyst, see U.S. Pat. No. 4,367,342. Hydrogen peroxide is another oxidizing agent useful for the preparation of epoxides. Olefin epoxidation using hydrogen peroxide and a titanium silicate zeolite is demonstrated in U.S. Pat. No. 4,833,260. One disadvantage of both of these processes is the need to pre-form the oxidizing agent prior to reaction with olefin.

Another commercially practiced technology is the direct epoxidation of ethylene to ethylene oxide by reaction with oxygen over a silver catalyst. Unfortunately, the silver catalyst has not proved very useful in epoxidation of higher olefins. Therefore, much current research has focused on the direct epoxidation of higher olefins with oxygen and hydrogen in the presence of a catalyst. In this process, it is believed that oxygen and hydrogen react in situ to form an oxidizing agent. Thus, development of an efficient process (and catalyst) promises less expensive technology compared to the commercial technologies that employ pre-formed oxidizing agents.

Many different catalysts have been proposed for use in the direct epoxidation of higher olefins. For example, JP 4-352771 discloses the epoxidation of propylene oxide from the reaction of propylene, oxygen, and hydrogen using a catalyst containing a Group VIII metal such as palladium on a crystalline titanosilicate. U.S. Pat. No. 5,859,265 discloses a catalyst in which a platinum metal, selected from Ru, Rh, Pd, Os, Ir and Pt, is supported on a titanium or vanadium silicalite. Additionally, it is disclosed that the catalyst may also contain additional elements, including Fe, Co, Ni, Re, Ag, or Au.

One disadvantage of the described direct epoxidation catalysts is that they are prone to ring-open the epoxide product under standard reaction conditions to form less desirable ring-opened by-products such as glycols or glycol ethers. U.S. Pat. No. 6,008,388 describes a direct olefin epoxidation process in which the selectivity for the reaction of olefin, oxygen, and hydrogen in the presence of a noble metal-modified titanium zeolite is greatly enhanced by the addition of a nitrogen compound to the reaction mixture. Also, increasing the catalyst activity as well as maximizing the catalyst life are important objectives in order to achieve an economical process. As with any chemical process, it is desirable to develop new direct epoxidation methods and catalysts.

In sum, new processes for the direct epoxidation of olefins are needed. Especially desirable are processes that increase activity, selectivity to the epoxide, as well as improving catalyst life. I have discovered an effective, convenient epoxidation process that reduces unwanted ring-opened products, increases catalyst activity, and improves catalyst life.

SUMMARY OF THE INVENTION

The invention is an olefin epoxidation process that comprises reacting olefin, oxygen, and hydrogen in the presence of a modifier and a catalyst comprising a noble metal and titanium zeolite. The modifier is either (a) calcium carbonate in the presence of carbon dioxide or (b) ammonium bicarbonate. This process surprisingly gives significantly reduced ring-opened by-products, and increased catalyst activity and life compared to processes that do not use the modifier.

DETAILED DESCRIPTION OF THE INVENTION

The process of the invention employs a catalyst that comprises a noble metal and titanium zeolite. Suitable titanium zeolites are those crystalline materials having a porous molecular sieve structure with titanium atoms substituted in the framework. The choice of titanium zeolite employed will depend upon a number of factors, including the size and shape of the olefin to be epoxidized. For example, it is preferred to use a relatively small pore titanium zeolite such as a titanium silicalite if the olefin is a lower aliphatic olefin such as ethylene, propylene, or 1-butene. Where the olefin is propylene, the use of a TS-1 titanium silicalite is especially advantageous. For a bulky olefin such as cyclohexene, a larger pore titanium zeolite such as a titanium zeolite having a structure isomorphous with zeolite beta may be preferred.

Titanium zeolites comprise the class of zeolitic substances wherein titanium atoms are substituted for a portion of the silicon atoms in the lattice framework of a molecular sieve. Such substances are well known in the art.

Particularly preferred titanium zeolites include the class of molecular sieves commonly referred to as titanium silicalites, particularly "TS-1" (having an MFI topology analogous to that of the ZSM-5 aluminosilicate zeolites), "TS-2" (having an MEL topology analogous to that of the ZSM-11 aluminosilicate zeolites), and "TS-3" (as described in Belgian Pat. No. 1,001,038). Titanium-containing molecular sieves having framework structures isomorphous to zeolite beta, mordenite, ZSM48, ZSM-12, and MCM-41 are also suitable for use. The titanium zeolites preferably contain no elements other than titanium, silicon, and oxygen in the lattice framework, although minor amounts of boron, iron, aluminum, sodium, potassium, copper and the like may be present.

Preferred titanium zeolites will generally have a composition corresponding to the following empirical formula $xTiO_2(1-x)SiO_2$ where x is between 0.0001 and 0.5000. More preferably, the value of x is from 0.01 to 0.125. The molar ratio of Si:Ti in the lattice framework of the zeolite is advantageously from 9.5:1 to 99:1 (most preferably from 9.5:1 to 60:1). The use of relatively titanium-rich zeolites may also be desirable.

The catalyst employed in the process of the invention also contains a noble metal. While any of the noble metals can be utilized (i.e., gold, silver, platinum, palladium, iridium, ruthenium, osmium), either alone or in combination, palladium is particularly desirable. Typically, the amount of noble metal present in the catalyst will be in the range of from 0.01 to 20 weight percent, preferably 0.05 to 10 weight percent.

The manner in which the noble metal is incorporated into the catalyst is not considered to be particularly critical. For example, the noble metal may be supported on the titanium zeolite by impregnation, adsorption, ion-exchange, precipitation. Alternatively, the noble metal may be first supported on another support such as an inorganic oxide, inorganic chloride, carbon, or organic polymer resins, or the like, and then physically mixed with the titanium zeolite. Preferred inorganic oxides include oxides of Group 2, 3, 4, 5, 6, 13, or 14 elements. Particularly preferred inorganic oxide supports include silica, alumina, titania, zirconia, niobium oxides, tantalum oxides, molybdenum oxides, tungsten oxides, amorphous titania-silica, amorphous zirconia-silica, amorphous niobia-silica, and the like. Preferred organic polymer resins include polystyrene, styrene-divinylbenzene copolymers, crosslinked polyethyleneimines, and polybenzimidizole. Suitable supports also include organic polymer resins grafted onto inorganic oxide supports, such as polyethylenimine-silica. Preferred supports also include carbon. Particularly preferred supports include carbon, silica, silica-aluminas, titania, zirconia, and niobia.

There are no particular restrictions regarding the choice of noble metal compound used as the source of the noble metal. For example, suitable compounds include the nitrates, sulfates, halides (e.g., chlorides, bromides), carboxylates (e.g. acetate), and amine complexes of noble metals.

Similarly, the oxidation state of the noble metal is not considered critical. In the case of palladium for instance, the palladium may be in an oxidation state anywhere from 0 to +4 or any combination of such oxidation states. To achieve the desired oxidation state or combination of oxidation states, the noble metal compound may be fully or partially pre-reduced after addition to the catalyst. Satisfactory catalytic performance can, however, be attained without any pre-reduction.

After noble metal incorporation, the catalyst is recovered. Suitable catalyst recovery methods include filtration and washing, rotary evaporation and the like. The catalyst is typically dried at a temperature greater than about 50° C. prior to use in epoxidation. The drying temperature is preferably from about 50° C. to about 300° C. The catalyst may additionally comprise a binder or the like and may be molded, spray dried, shaped or extruded into any desired form prior to use in epoxidation. The catalyst may be optionally thermally treated in a gas such as nitrogen, helium, vacuum, hydrogen, oxygen, air, or the like. The thermal treatment temperature is typically from about 50 to about 550° C.

The epoxidation process of the invention comprises reacting olefin, oxygen, and hydrogen in the presence of a modifier and the catalyst. The modifier is either (a) calcium carbonate in the presence of carbon dioxide or (b) ammonium bicarbonate. The ammonium bicarbonate or calcium carbonate can be simply added to the reaction medium in which the epoxidation is being performed. The ammonium bicarbonate or calcium carbonate may be added all at once either prior to or following initiation of epoxidation or may be added in an incremental or continuous manner. Ammonium carbonate may also be formed in-situ during the epoxidation reaction.

Sufficient ammonium bicarbonate is necessary to be effective to improve catalyst activity and selectivity to the epoxide as compared to the same reaction carried out under similar conditions in the absence of the ammonium bicarbonate. The amount of ammonium bicarbonate is in the range of from about 10 ppm to about 50,000 ppm (as measured by the weight of ammonium bicarbonate to the weight of the entire reaction mixture), and preferably in the range of from about 100 ppm to about 1500 ppm.

The amount of calcium carbonate used is not believed to be particularly critical, but at a minimum should be effective to improve catalyst activity and selectivity to the epoxide as compared to the same reaction carried out under similar conditions in the absence of the calcium carbonate. Preferably, the amount of calcium carbonate is in the range of from about 50 ppm to about 10,000 ppm (as measured by the weight of calcium carbonate to the weight of the entire reaction mixture), and most preferably in the range of from about 150 ppm to about 5000 ppm.

When the modifier contains calcium carbonate, it must be used in the presence of carbon dioxide. The carbon dioxide will typically be added to the reaction mixture along with the other reaction gases, comprising oxygen, hydrogen, and light olefins such as propylene which may be introduced in the gas phase. Although the amount of carbon dioxide is not critical, the amount of carbon dioxide in the gas is typically in the range of from about 0.01 volume % to about 90 volume % (as measure by volume $CO_2$ per total volume of all gases introduced into the reactor), and preferably from about 0.05 volume % to about 5 volume %.

The epoxidation process of the invention comprises contacting an olefin, oxygen, and hydrogen in the presence of the modifier and the catalyst. Suitable olefins include any olefin having at least one carbon-carbon double bond, and generally from 2 to 60 carbon atoms. Preferably the olefin is an acyclic alkene of from 2 to 30 carbon atoms; the process of the invention is particularly suitable for epoxidizing $C_2$–$C_6$ olefins. More than one double bond may be present, as in a diene or triene for example. The olefin may be a hydrocarbon (i.e., contain only carbon and hydrogen atoms) or may contain functional groups such as halide, carboxyl, hydroxyl, ether, carbonyl, cyano, or nitro groups, or the like. The process of the invention is especially useful for converting propylene to propylene oxide.

Oxygen and hydrogen are also required for the process of the invention. Although any sources of oxygen and hydrogen are suitable, molecular oxygen and molecular hydrogen are preferred. The molar ratio of hydrogen to oxygen can usually be varied in the range of $H_2:O_2=1:100$ to $5:1$ and is especially favorable at 1:5 to 2:1. The molar ratio of oxygen to olefin is usually 1:1 to 1:20, and preferably 1:1.5 to 1:10. Relatively high oxygen to olefin molar ratios (e.g., 1:1 to 1:3) may be advantageous for certain olefins.

In addition to olefin, oxygen and hydrogen, an inert gas carrier may be preferably used in the process. As the carrier gas, any desired inert gas can be used. Suitable inert gas carriers include noble gases such as helium, neon, and argon in addition to nitrogen and carbon dioxide. Saturated hydrocarbons with 1–8, especially 1–6, and preferably with 1–4 carbon atoms, e.g., methane, ethane, propane, and n-butane, are also suitable. Nitrogen and saturated $C_1$–$C_4$ hydrocarbons are the preferred inert carrier gases. Mixtures of the listed inert carrier gases can also be used. The molar ratio of olefin to carrier gas is usually in the range of 100:1 to 1:10 and especially 20:1 to 1:10.

Specifically in the epoxidation of propylene according to the invention, propane can be supplied in such a way that, in the presence of an appropriate excess of carrier gas, the explosive limits of mixtures of propylene, propane, hydrogen, and oxygen are safely avoided and thus no explosive mixture can form in the reactor or in the feed and discharge lines.

The amount of catalyst used may be determined on the basis of the molar ratio of the titanium contained in the titanium zeolite to the olefin that is supplied per unit time. Typically, sufficient catalyst is present to provide a titanium/olefin per hour molar feed ratio of from 0.0001 to 0.1.

Depending on the olefin to be reacted, the epoxidation according to the invention can be carried out in the liquid phase, the gas phase, or in the supercritical phase. The process of the invention is preferably carried out in the liquid-phase. When a liquid reaction medium is used, the catalyst is preferably in the form of a suspension or fixed-bed. The process may be performed using a continuous flow, semi-batch or batch mode of operation.

If epoxidation is carried out in the liquid phase, it is advantageous to work at a pressure of 1–100 bars and in the presence of one or more solvents. Suitable solvents include, but are not limited to, lower aliphatic alcohols such as methanol, ethanol, isopropanol, and tert-butanol, or mixtures thereof, and water. Fluorinated alcohols can be used. It is also possible to use mixtures of the cited alcohols with water.

The following examples merely illustrate the invention. Those skilled in the art will recognize many variations that are within the spirit of the invention and scope of the claims.

EXAMPLE 1: CATALYST PREPARATION

TS-1 can be made according to any known literature procedure. See, for example, U.S. Pat. No. 4,410,501, DiRenzo, et. al., *Microporous Materials* (1997), Vol. 10, 283, or Edler, et. al., *J. Chem. Soc., Chem. Comm.* (1995), 155.

Catalyst 1A: TS-1 (20 g, 1.6 weight % Ti), [Pd(NH$_3$)$_4$](NO$_3$)$_2$](2.542 g of a 5 weight percent Pd solution in water, Strem Chemicals), and deionized water (80 g) are placed in a 250-mL single-neck round-bottom flask forming a pale white mixture. The flask is connected to a 15-inch cold water condenser and then blanketed with nitrogen at a 150 cc/min flow rate. The flask is inserted into an oil bath at 80° C. and the reaction slurry is stirred. After stirring for 24 hours, the slurry is filtered under pressurized N$_2$, washed with deionized water (150 mL, three times), and then the solid is dried in a vacuum oven at 50° C. overnight. The solid catalyst is then calcined in 4% oxygen (remainder nitrogen) at 150° C. for 4 hours. Measured Pd loading of the catalyst is 0.47 wt.%.

Catalyst 1B: Pd incorporation onto TS-1 is conducted according to the same procedure as for Catalyst 1A, except that 10 g TS-1, 0.8 g of [Pd(NH$_3$)$_4$](NO$_3$)$_2$](5 wt. % Pd solution in water), and 40 g deionized water is used. Measured Pd loading of the catalyst is 0.31 wt.%.

EXAMPLE 2: PROPYLENE EPOXIDATION STUDIES WITH AND WITHOUT MODIFIERS

To evaluate the performance of the catalysts prepared in Example 1 in the presence of modifiers, the epoxidation of propylene using oxygen and hydrogen is carried out. The following procedure is employed.

The catalyst is slurried into 100 grams of methanol/water mixture (75 wt.% MeOH; 25 wt.% H$_2$O) and added to the reactor system, consisting of a 300-mL high-pressure reactor and a 1000-mL methanol saturator. The methanol/water mixture does not contain any modifier for runs 2A–2C, but contains a modifier for runs 2D–2I (Table 1 lists the amount of modifier used for each run). The slurry is then heated to 60° C. and stirred at 1500 rpm. A gaseous feed consisting of 10% propylene, 4% oxygen, 1% hydrogen and 85% nitrogen is added to the system with a total flow of 1200 cc/min and a reactor pressure of 300 psi. Both the gas and liquid phase samples are collected and analyzed by G.C.

The epoxidation results, in Table 2, show that the use of ammonium bicarbonate modifier (Run 2D) leads to an unexpected increase in catalyst activity and a decrease in the amount of ring-opened by-products as shown by higher PO/POE ratio compared to unmodified runs 2A–C. "POE" means PO equivalents, which include propylene oxide (PO), propylene glycol (PG), dipropylene glycol (DPG), 1-methoxy-2-propanol (PM-1), 2-methoxy-1-propanol (PM-2), and acetol. Also, the use of other ammonium or carbonate containing compounds fails to produce similar results as seen in runs 2EI.

Interestingly, run 2D shows little if any loss in catalyst activity over the 90-hour epoxidation run compared to runs 2A–C, thus demonstrating increased catalyst life.

EXAMPLE 3: PROPYLENE EPOXIDATION STUDIES WITH AND WITHOUT MODIFIERS IN PRESENCE OF CARBON DIOXIDE

To evaluate the performance of the catalysts prepared in Example 1 with and without modifiers in the presence of carbon dioxide, the epoxidation of propylene using oxygen and hydrogen is carried out. The following procedure is employed.

The catalyst is slurried into 100 grams of methanol/water mixture (75 wt.% MeOH; 25 wt.% H$_2$O) and added to the reactor system, consisting of a 300-mL high-pressure reactor and a 1000-mL methanol saturator. The methanol/water mixture does not contain any modifier for run 3A, but contains a modifier for runs 3B–D (run 3B uses 2000 ppm CaCO$_3$; run 3C uses 400 ppm KHCO$_3$; and run 3D uses 400 ppm tetrapropylammonium hydroxide (TPAOH)). The slurry is then heated to 60° C. and stirred at 1500 rpm. A gaseous feed consisting of 10% propylene, 4% oxygen, 1% hydrogen, 84.9% nitrogen, and 0.1% carbon dioxide is added to the system with a total flow of 1200 cc/min and a reactor pressure of 300 psi. Both the gas and liquid phase samples are collected and analyzed by G.C.

The epoxidation results, in Table 3, show that the use of calcium carbonate in the presence of carbon dioxide (Run 3B) leads to an unexpected increase in catalyst activity and higher PO/POE ratio compared to runs using just carbon dioxide (Run 3A) or just calcium carbonate (Run 2I). Also, the use of other modifier compounds fails to produce similar results, as seen in runs 3C–D. Also, run 3B shows little if any loss in catalyst activity over the 45-hour epoxidation run compared to run 3A, thus demonstrating increased catalyst life.

TABLE 1

Amount of Modifier used in Epoxidation Reactions.

| Run # | Modifier | Modifier Amount (ppm)[a] |
|---|---|---|
| 2D | (NH$_4$)HCO$_3$ | 500 |
| 2E | (NH$_4$)H$_2$PO$_4$ | 500 |
| 2F | (NH$_4$)Br | 500 |
| 2G | NaHCO$_3$ | 500 |
| 2H | KHCO$_3$ | 250 |
| 2I | CaCO$_3$ | 500 |

TABLE 1-continued

Amount of Modifier used in Epoxidation Reactions.

| Run # | Modifier | Modifier Amount (ppm)[a] |
| --- | --- | --- |

[a]Modifier amount is the amount of modifier compound in the methanol/water mixture.

TABLE 2

Propylene Epoxidation for Modified and Non-modified Runs.

| Run # | Catalyst | Run time (h) | Modifier | Mean PO Productivity (g PO/g cat/h) | Mean POE[a] Productivity (g POE/g cat/h) | PO/POE (%) |
| --- | --- | --- | --- | --- | --- | --- |
| 2A* | 1A | 88.5 | — | 0.20 | 0.23 | 85 |
| 2B* | 1B | 64.5 | — | 0.21 | 0.30 | 72 |
| 2C*[b] | 1B | 70.5 | — | 0.13 | 0.14 | 92 |
| 2D | 1A | 90 | (NH$_4$)HCO$_3$ | 0.31 | 0.35 | 90 |
| 2E* | 1A | 54 | (NH$_4$)H$_2$PO$_4$ | 0.18 | 0.24 | 77 |
| 2F* | 1A | 54 | (NH$_4$)Br | 0.19 | 0.21 | 89 |
| 2G* | 1B | 64.5 | NaHCO$_3$ | 0.018 | 0.021 | 89 |
| 2H* | 1B | 40.5 | KHCO$_3$ | 0.02 | 0.023 | 90 |
| 2I*[b] | 1B | 70.5 | CaCO$_3$ | .044 | .047 | 95 |

*Comparative Example
[a]POE = PO + ring-opened by-products (PG, DPG, PM-1, PM-2, and acetol). g POE (grams POE) = grams PO$_{final}$ + grams PO$_{converted\ to\ ring-opened\ by-products}$.
[b]Run is conducted at 45° C.

TABLE 3

Propylene Epoxidation Results for Carbonates plus CO$_2$.

| Run # | Catalyst | Run time (h) | Modifier | Mean PO Productivity (g PO/g cat/h) | Mean POE[a] Productivity (g POE/g cat/h) | PO/POE (%) |
| --- | --- | --- | --- | --- | --- | --- |
| 3A* | 1A | 52.5 | 0.1 vol % CO$_2$ | 0.20 | 0.26 | 78 |
| 3B | 1A | 45 | 2000 ppm CaCO$_3$ + 0.1 vol % CO$_2$ | 0.24 | 0.27 | 88 |
| 3C* | 1A | 69 | 400 ppm KHCO$_3$ + 0.1 vol % CO$_2$ | 0.033 | 0.035 | 94 |
| 3D* | 1A | 55 | 400 ppm TPAOH + 0.1 vol % CO$_2$ | 0.11 | 0.12 | 90 |

*Comparative Example
[a]POE = PO + ring-opened by-products (PG, DPG, PM-1, PM-2, and acetol). g POE (grams POE) = grams PO$_{final}$ + grams PO$_{converted\ to\ ring-opened\ by-products}$.

I claim:

1. A process for producing an epoxide comprising reacting an olefin, oxygen, and hydrogen in the presence of a modifier and a catalyst comprising a noble metal and titanium zeolite, wherein the modifier is (a) calcium carbonate in the presence of carbon dioxide or (b) ammonium bicarbonate.

2. The process of claim 1 wherein the titanium zeolite is titanium silicalite.

3. The process of claim 1 wherein the titanium zeolite is TS-1.

4. The process of claim 1 wherein the catalyst is comprised of from 0.01 to 10 weight percent noble metal.

5. The process of claim 1 wherein the noble metal is palladium.

6. The process of claim 1 wherein the olefin is a $C_2$–$C_6$ olefin.

7. The process of claim 1 wherein the olefin is propylene.

8. The process of claim 1 wherein the modifier is calcium carbonate in the presence of carbon dioxide.

9. The process of claim 1 wherein the modifier is ammonium bicarbonate.

10. The process of claim 1 further comprising a solvent selected from the group consisting of methanol, ethanol, isopropanol, and tert-butanol, and water.

11. A process comprising reacting propylene, hydrogen and oxygen in a solvent in the presence of ammonium bicarbonate and a catalyst comprising palladium and a titanium silicalite.

12. The process of claim 11 wherein the titanium silicalite is TS-1.

13. The process of claim 11 wherein the catalyst is comprised of from 0.01 to 10 weight percent palladium.

14. The process of claim 11 wherein the solvent is selected from the group consisting of methanol, ethanol, isopropanol, tert-butanol, and water.

15. A process comprising reacting propylene, hydrogen and oxygen in a solvent in the presence of a modifier and a catalyst comprising palladium and a titanium silicalite, wherein the modifier is calcium carbonate in the presence of carbon dioxide.

16. The process of claim 15 wherein the titanium silicalite is TS-1.

17. The process of claim 15 wherein the catalyst is comprised of from 0.01 to 10 weight percent palladium.

18. The process of claim 15 wherein the solvent is selected from the group consisting of methanol, ethanol, isopropanol, tert-butanol, and water.

* * * * *